United States Patent [19]

Brackenridge et al.

[11] Patent Number: 4,740,629

[45] Date of Patent: Apr. 26, 1988

[54] BROMINATION PROCESS

[75] Inventors: David R. Brackenridge, Baton Rouge, La.; Bonnie G. McKinnie, Magnolia, Ark.

[73] Assignee: Ethyl Corporation, Richmond, Va.

[21] Appl. No.: 69,639

[22] Filed: Jul. 6, 1987

Related U.S. Application Data

[63] Continuation-in-part of Ser. No. 854,015, Apr. 21, 1986.

[51] Int. Cl.$^4$ .................... C07C 41/22; C07C 43/115
[52] U.S. Cl. .................................. 568/639; 568/776; 568/637
[58] Field of Search ............... 568/639, 637, 630, 776

[56] References Cited

U.S. PATENT DOCUMENTS 3,965,197 6/1976 Stepniczk ........................ 568/776
4,287,373 9/1981 Garman et al. ................... 568/639

Primary Examiner—Werren B. Lone
Attorney, Agent, or Firm—Donald L. Johnson; John F. Sieberth

[57] ABSTRACT

A process for partially brominating non-condensing ring aromatics (e.g. diphenyl ether) in the absence of a solvent by adding the polyaromatic to a stoichiometric excess of liquid bromine containing a zirconium halide catalyst. Product containing three bromine atoms per benzene ring (e.g., hexabromodiphenyl ether) is formed in high selectivity by keeping the reaction mixture below a threshold temperature at which higher bromine substitution occurs.

9 Claims, No Drawings

BROMINATION PROCESS

REFERENCE TO RELATED APPLICATION

This is a continuation-in-part of prior copending application Ser. No. 854,015, filed Apr. 21, 1986.

BACKGROUND OF THE INVENTION

Procedures for making perbrominated polyphenylene ethers are known. For example, decabromodiphenyl ether (referred to as "Decabrom") is a commercial fire retardant. It can be made by adding molten diphenyl ether to a large stoichiometric excess of liquid bromine containing a halogenation catalyst such as aluminum halide (U.S. Pat. NO. 3,965,197). Although it is not a solvent, the large excess of bromine acts as a liquid medium in which the product is suspended and from which it can be readily recovered.

In some uses it is preferred to have only a partially brominated flame retardant because it might have more desirable physical properties in a particular substrate. For example a partially brominated diphenyl ether is sold as octabromodiphenyl ether (referred to as "Octabrom") although its actual composition is a mixture of partially brominated diphenyl ether. The commercial grade product contains about 6-9 bromine atoms per molecule.

Using the aluminum halide bromination catalyst as practiced in U.S. Pat. No. 3,965,197, the degree of bromination can only be limited by restricting the amount of bromine at about the stoichiometric amount required to insert eight bromine atoms per molecule. Also the product is very colored (yellow to brown) requiring extensive purification if a light colored product is required.

SUMMARY OF THE INVENTION

In accordance with one embodiment, non-condensed ring polyaromatics are partially brominated to contain about 3-4 bromine atoms per benzene ring by conducting the reaction in a large stoichiometric excess of liquid bromine and using a zirconium halide catalyst which may be promoted with a small amount of iron. The product tends to be much lighter colored than that obtained by adding a stoichiometric amount of bromine to the same polyaromatic compound.

In accordance with another embodiment, it has been discovered that by suitably controlling the temperature of the reaction it is possible to introduce three bromine atoms per benzene ring with high selectivity.

DESCRIPTION OF THE PREFERRED EMBODIMENTS

A preferred embodiment of the invention is a process for making a partially brominated polyphenylene ether, said process comprising reacting said polyphenylene ether with bromine in the presence of a zirconium halide catalyst, at a temperature from about 10° C. up to reflux.

Polyphenylene ethers as used herein means a compound having two or more benzene rings connected through an oxygen atom. They can be represented by the formula

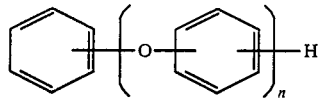

wherein n is an integer having a value of at least 1 up to 20 or more. Some examples of these are:
diphenyl ether,
1,4-diphenoxybenzene,
1,3-diphenoxybenzene,
1,2-diphenoxybenzene,
tetra-(p-phenyleneoxy)benzene wherein
"tetra-(p-phenyleneoxy)" means four of the above

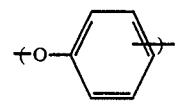

groups bonded in the para position, i.e.

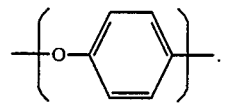

The most important polyphenylene ethers are diphenyl ether and the various isomers of diphenoxybenzene, especially 1,4-diphenoxybenzene.

Another preferred embodiment of the invention is a process for making a partially brominated non-condensed ring polyaromatic other than a partially brominated polyphenylene ether, said process comprising reacting said non-condensed ring polyaromatic with bromine in the presence of a zirconium halide catalyst, at a temperature from about 10° C. up to reflux. The preferred polyaromatics of this type can be represented by the formula

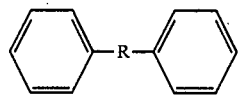

wherein R is an alkylene group of up to 6 or more carbon atoms, an oxyalkylene group (—O—R—) of up to 6 or more carbon atoms, an oxyalkyleneoxy group (—O—R—O—) of up to 6 or more carbon atoms, a sulfur atom, or a carbon-to-carbon single bond. Some examples of these compounds are:
diphenylmethane,
1,2-diphenylethane,
benzylphenylether,
1,2-diphenoxyethane,
diphenylsulfide
diphenyl,
1,4-diphenylbutane.

The amount of bromine used is an amount in excess of the stoichiometric amount required to substitute four bromine atoms per benzene ring. For example with diphenyl ether the stoichiometric amount is 8 moles of bromine per mole of diphenyl ether. With diphenoxybenzene the stoichiometric amount is 12 moles of bromine per mole of diphenoxybenzene.

The stoichiometric excess can range from about 25% up to 500% or more. This means that the amount of bromine ranges from about 5 to 24 moles, more preferably 6 to 24 moles per equivalent of non-condensed ring polyaromatic wherein an equivalent of non-condensed ring polyaromatic is the molecular weight divided by the number of benzene rings per molecule. Thus with diphenoxybenzene the amount of bromine can range from about 15–72 moles, more preferably 18–72 moles per mole of diphenoxybenzene. With diphenyl ether the amount of bromine can range from about 10 to 48 moles, more preferably 12 to 48 moles of bromine per mole of diphenyl ether.

The excess bromine acts as a liquid reaction medium in which the bromination is conducted. No other solvent is required and it is preferred that no other solvent be used since such use can contaminate the product.

The critical feature of the invention is the use of a zirconium halide catalyst rather than the conventional aluminum halide catalyst which cause perbromination. When aluminum halides are used a partially brominated product will not result when using an excess amount of bromine. With aluminum halides the amount of bromine must be restricted to close to the stoichiometric amount.

Any zirconium halide can be used such as zirconium chloride, zirconium bromide, zirconium fluoride and mixtures thereof. The most readily available zirconium halide is zirconium tetrachloride. In the reaction mixture the catalytic species is very likely zirconium tetrabromide since large amounts of hydrogen bromide are evolved which can convert any of the zirconium tetrahalides to zirconium tetrabromide.

The amount of zirconium halide should be an amount which will catalyze the reaction of bromine with the polyphenylene ether to substitute bromine into the benzene rings. A useful range in which to operate is about 0.1–10 weight percent based on the amount of bromine. A more preferred range is about 0.3–5 weight percent based on the bromine charge.

The reaction is preferably conducted by charging the bromine and zirconium halide to a reaction vessel and then feeding the polyphenylene ether to the liquid bromine. The reaction temperature can range from below ambient (e.g. $-10°$ C.) up to reflux temperature under reaction conditions. Although bromine refluxes at about $59°$ at atmospheric pressure, the reaction may be conducted at above atmospheric pressure, for example 5 to 25 psig, under which conditions reflux temperature will increase.

More preferably the reaction is started at the temperature of the charged bromine (e.g. $20°–30°$ C.) and is permitted to rise during the course of the reaction to a higher temperature (e.g. $30°–40°$ C.). Heat is then supplied to the reaction mixture to bring the mixture to reflux and speed up the reaction rate.

The non-condensed ring polyaromatic may be added to the bromine as a solid or as a liquid. For ease of operation the non-condensed ring polyaromatic is preferably added molten even if this temperature is higher than the bromine temperature or even higher than bromine reflux temperature. For example, diphenyl ether melts at about $27°$ C. so it is typically fed to the bromine at about $28°–35°$ C. to prevent freeze up in the feed conduit.

The non-condensed ring polyaromatic is added to the bromine over a period of time. Feed time depends on scale and ability to control temperature and handle hydrogen bromide evolution. On a laboratory scale the addition requires about 15 minutes to one hour. On a commercial scale, the reaction could take about 2–8 hours or longer.

After completion of the non-condensed ring polyaromatic addition, the reaction mixture can be held for a period to assure the desired degree of bromination has been achieved. A ride period of about 4–5 hours at or near reflux is beneficial. When an iron promoter is used this time can be shortened.

Product can be recovered by any of several conventional methods. For example the reaction mixture can be mixed with water and the excess bromine distilled out. The product can then be recovered from the water by filtration or centrifugation and then dried and ground to the desired particle size. Alternatively, a solvent such as toluene can be added to the water-product mixture to dissolve the product. The solvent phase can be separated and the solvent distilled out leaving the product which is then crushed and ground to a fine powder.

The manner in which the above embodiment of the process can be conducted is shown in the following examples:

EXAMPLE 1

In a glass reaction vessel was placed 200 grams (1.25 moles, 56% stoichiometric excess based on diphenyl ether) of bromine and 1.7 grams of $ZrCl_4$. The vessel was fitted with a stirrer and reflux condenser which was vented through a mineral oil bubbler to a caustic scrubber to absorb evolved hydrogen bromide. Molten ($28°$ C.) diphenyl ether (17 grams, 0.1 mole) was fed to the stirred bromine at $21–22°$ C. over a 28 minute period. Heat was applied to increase the reaction temperature to reflux. Total reaction time was 4.13 hours and final temperature was $68.7°$ C. Water (120 ml) was then added to terminate the reaction. The excess bromine was distilled from the mixture to a pot temperature of about $100°$ C. Residual bromine was purged with nitrogen. Toluene (90 ml) was added to dissolve the product. Aqueous sodium sulfite (10 ml, 10 weight percent $Na_2SO_3$) was mixed with the toluene solution to remove trace bromine. The toluene layer was separated, washed with 100 ml hot water and dried over magnesium sulfate. After filtration the toluene was removed under vacuum to a temperature of $130°$ C. at about 2 Torr. The product was cooled and crushed and analyzed by gas chromatography (area percent by GC) as follows:

| | |
|---|---|
| Hexabrom[1] | 27.8% |
| Heptabrom[1] | 50.3% |
| Octabrom[1] | 17.2% |
| Nonabrom[1] | 4.4% |
| Decabrom[1] | 0.4% |

[1]diphenyl ether.

EXAMPLES 2–6

A series of reactions was conducted following the above general procedure with minor variations as follows:

TABLE 1

| Example | $ZrCl_4$[2] | Bromine[3] | DPE[1] Addition Time (min.) | DPE[1] Addition Temp. (°C.) | Total Reaction Time (hrs.) | Final Reaction Temp. |
|---|---|---|---|---|---|---|
| 2 | 14.6 | 100 | 25 | 20–21 | 3.58 | 64.5 |

TABLE 1-continued

| Example | ZrCl$_4$[2] | Bromine[3] | DPE[1] Addition Time (min.) | DPE[1] Addition Temp. (°C.) | Total Reaction Time (hrs.) | Final Reaction Temp. |
|---|---|---|---|---|---|---|
| 3 | 7.3 | 100 | 24 | 19-24 | 5.5 | 64.5 |
| 4 | 4.3 | 100 | 30 | 19-21 | 5.0 | 65.0 |
| 5 | 4.3 | 75 | 14 | 20-26 | 5.0 | 69.0 |
| 6 | 2.4 | 50 | 30 | 19-25 | 4.0 | 69.9 |

[1] Diphenyl ether
[2] Mole percent based on diphenyl ether
[3] Percent stoichiometric excess based on converting diphenyl ether to Octabrom

TABLE II

| | Product Analysis (Area percent by G.C.) | | | | |
|---|---|---|---|---|---|
| Example | Hexabrom | Heptabrom | Octabrom | Nonabrom | Decabrom |
| 2 | 10.4 | 49.2 | 24.1 | 13.3 | 3.0 |
| 3 | 4.9 | 38.6 | 30.7 | 21.3 | 4.5 |
| 4 | 4.2 | 32.6 | 35.7 | 21.1 | 6.3 |
| 5 | 6.2 | 35.0 | 37.9 | 18.2 | 2.7 |
| 6 | 16.5 | 45.0 | 28.2 | 9.0 | 1.3 |

As the above results demonstrate, the present process makes it possible to achieve partial bromination of a polyphenylene ether using a large stoichiometric excess of bromine as the only reaction medium.

In another embodiment of the invention the reaction rate is sharply increased while still controlling the degree of bromination to about 3-4 bromine atoms per benzene ring by conducting the process including a small promoter amount of iron. The iron is preferably added to the bromine in the form of iron particles such as iron powder. The amount of iron can range from about 0.01-1.0 gram atoms per gram moles of zirconium halide catalyst. A more preferred range is about 0.05-0.5 and still more preferably about 0.1-0.3 gram atoms of iron per mole of zirconium halide.

The following examples show the zirconium halide bromination process carried out with an iron promoter.

EXAMPLE 7

In a glass reaction vessel was placed 192.5 grams of bromine, 0.56 grams (0.0024 moles) zirconium chloride and 0.02 grams (0.00036 gram atoms) of iron powder. While stirring, 17 grams of molten diphenyl ether was added at 21°-27° C. over a 30 minute period. The reaction mixture was then heated to reflux (64° C.) and stirred until the amount of HBr evolved indicated that Octabrom had been formed. Total time from start of diphenyl ether feed was 3.2 hours.

The reaction was quenched with 150 ml of water and excess bromine was distilled out. A small amount (1.4 grams) of sodium sulfite in 50 ml water was added to decompose residual bromine. Then 100 ml of toluene was added to dissolve the product at about 85°-90° C. The organic layer was separated and washed with 150 ml of hot water and dried over magnesium sulfate. The mixture was filtered and the toluene distilled out under vacuum at 130°/1-2 Torr for 1 hour. The residual product (75.3 grams) analyzed by G.C. in area percent as follows:

| | |
|---|---|
| hexabrom - | 6.21% |
| heptabrom - | 48.9% |
| octabrom - | 26.95% |
| nonabrom - | 15.25% |
| decabrom - | 2.69% |

Average bromine atoms per molecule was 7.59.

EXAMPLE 8

An experiment was conducted following the general procedure of Example 7 but using 575.4 grams of bromine (3.6 moles), 1.46 grams of zirconium tetrachloride (0.0063 moles), 0.07 grams of iron powder (0.00125 gram atoms) and 51.0 grams of diphenyl ether (0.3 moles). The molten diphenyl ether was added over a 1.35 hour period at 20°-25° C. followed by reflux. Total reaction time was 3.3 hours. Product recovery was the same as before. Yield 223.4 grams. G.C. analysis was as follows:

| | |
|---|---|
| hexabrom - | 11.2% |
| heptabrom - | 52.54% |
| octabrom - | 24.19% |
| nonabrom - | 10.6% |
| decabrom - | 1.48% |

Average 7.39 bromine atoms per molecule. Melt range 72°-130° C.

As these results show, the use of an iron promoter with the zirconium halide catalyst gives about the same product distribution but achieves this in a much shorter time.

In still another preferred embodiment of this invention the zirconium halide catalyzed reaction is caused to selectively introduce three bromine atoms in the benzene rings of the non-condensed ring polyaromatic such as diphenyl ether. This is effected by controlling the reaction temperature so that it does not exceed a threshhold temperature at which higher bromine substitution occurs. In the case of diphenyl ether this threshhold temperature is 30° C. Preferably the temperature is kept at about 20 to about 26° C. throughout substantially the entire reaction period.

In conducting this embodiment of the invention without an ancillary solvent, it is preferred to employ at least about 50 mole percent excess of bromine over the stoichiometric amount required to substitute three bromine atoms per benzene ring. This stoichiometric excess may be as high as 500 percent or more although in most cases the excess will not exceed 200 percent. Preferably the amount of bromine used is about 75 to about 100 mole percent in excess of the stoichiometric equivalent.

Thus in the case of diphenyl oxide, the mole ratio of bromine to diphenyl oxide will be at least about 9:1 (and preferably about 10.5:1 to 12:1) when forming hexabrom in the absence of an ancillary solvent. When substituting three bromine atoms per ring in diphenoxybenzene or terphenyl by means of this embodiment, the mole ratio of bromine to the aromatic reactant will be at least about 13.5:1, and preferably about 15.7:1 to about 18:1.

The following examples illustrate this embodiment of the invention.

EXAMPLE 9

A 500 ml reaction flask was charged with bromine (383.6 g, 2,401M, 50.0 mole percent excess for Octabrom and ZrCl$_4$ (1.0 g, 0.0043M). The flask was fitted with a mechanical stirrer and glass thermowell and attached in series to a water condenser and a cold finger condenser (cooled to ~−30° C. using 50:50 isopropanol/ H₂O and dry ice). The gas exit of the cold finger condenser led to a three-way stopcock (for N₂ purging when necessary), then to a mineral oil bubbler, 500 ml safety trap and a tared caustic trap. The HBr evolved was directed by a dip-leg (no frit) to just below the caustic surface, to prevent significant gas pressure buildup in the system, with accompanying leaks through the various joints.

Molten diphenyl oxide (DPO) (34.0 g, 0.20M) was added over 0.77 hours at 17°–18° C. (external heat sink). A GC sample was removed and stirring was continued for an additional hour. A second GC sample was removed and the mixture was then brought to reflux and sampled periodically. The product composition at various stages during the run is summarized in Table III.

to <25° C. To re-liquefy the mixture, additional bromine was added, giving a *total* bromine charge of 1452.2 g (9.09M, 102 mole percent excess for hexabrom. The mixture was then stirred at 21°–23° C.; after a total of 4.67 hrs., a slow N₂ flush of the overhead system was started. After 5.75 hrs (including 2.08 hrs addition), the approximate amount of HBr gas equivalent to hexabrom formation was obtained in the caustic trap; the reaction was stopped by addition of water (1:1).

The excess bromine was distilled overhead and converted (in caustic solution) to sodium bromide/sodium hypobromite. When most of the bromine had been distilled overhead, product deposition began, with formation of granular solids. Subsequent difficulty in stirring necessitated addition of chlorobenzene (~1:1) to solubilize the product. The last traces of free bromine were removed by addition of sodium sulfite (6.5 g) in water

TABLE III

| Hrs. | Run Stage | Product Analysis (Area percent by G.C.)* | | | | | | |
|---|---|---|---|---|---|---|---|---|
| | | Tetrabrom | Pentabrom | Hexabrom | Heptabrom | Octabrom | Nonabrom | Decabrom |
| 0.77 | End of DPO feed (17° C.) | 1.9 | 45.9 | 51.6 | 0.6 | — | — | — |
| 1.72 | After 1 hr at 17° C. | 0.1 | 32.6 | 66.3 | 1.0 | — | — | — |
| 2.80 | 67.5° C. pot | — | 0.2 | 61.7 | 34.9 | 2.9 | 0.4 | — |
| 3.80 | 68.4° C. pot | — | — | 46.1 | 43.8 | 8.8 | 1.3 | — |
| 4.80 | 69.2° C. pot | — | — | 35.6 | 48.0 | 13.9 | 2.6 | trace |
| 5.80 | 70.9° C. pot | — | — | 26.7 | 49.4 | 19.2 | 4.6 | trace |

*10 meter × 0.53 mm wide-bore capillary column (DB-1 stationary phase)

EXAMPLE 10

The same equipment described in Example 9 was used except that magnetic stirring was employed. Bromine (385.9 g, 2.415M, 101.3 mole percent excess for Hexabrom) and ZrCl₄ (1.2 g, 0.0052M) were charged to the reactor, and molten diphenyl oxide (34.1 g, 0.20M) was added over 1.08 hours at 19°–26° C. The reaction mixture was then stirred at 20°–23° C. with periodic sampling for GC analysis. After a total of 3.25 hours (including addition), the reaction was terminated. The final product contained an average of 5.92 Br/DPO. The product melting range was 127°–158° C., with a 92.4 percent yield for Hexabrom. The product composition at various times during the bromination is given in Table IV.

TABLE IV

| Hrs. | Run Stage | Product Analysis (Area % by G. C.) | | | |
|---|---|---|---|---|---|
| | | Tetra-brom | Pentabrom | Hexa-brom | Hepta-brom |
| 1.25 | End of DPO feed + 0.25 hrs. | 2.02 | 31.98 | 64.42 | 1.59 |
| 2.25 | | — | 24.518 | 72.97 | 2.47 |
| 3.25 | | — | 10.334ᵃ | 86.73 | 2.85 |

ᵃSlow N₂ flush (between condenser and oil bubbler) of overhead system started at t = 2.38 hrs.

EXAMPLE 11

A 2-liter reaction flask equipped with mechanical stirrer, thermowell and the condenser and overhead setup as per Example 9 was charged with bromine (1086.4 g, 6.80M) and ZrCl₄ (3.75 g, 0.016M). Molten diphenyl oxide (127.7 g, 0.750M) was added over 2.08 hrs. at 20°–21° C. (external cooling bath).

The cooling bath was then removed, but solids deposition and a consequent exotherm to 26.5° C. necessitated use of the bath to cool the semi-solid reaction mass (50 ml). Agitation for <1 minute reacted out the bromine and gave a nearly colorless organic solution. The aqueous layer was removed and the organic layer was washed with water (500 ml×2). The warm organic solution (~80° C.) was transferred to a separatory funnel, where the last few milliliters of visible water were separated. The organic solution was dried briefly with MgSO₄ (5 g), filtered and solvent stripped, with a final strip at 130° C./1–2 mm. for 1 hour. The product (481.3 g, 99.7 percent yield for hexabrom) melted at 138°–160° C. The product was found to have excellent color characteristics (lack of color). The amount of transmission of light (at 400 nm) through a 10% by weight solution of the product in toluene in a 10 cm cell was used as the test criterion. Analysis of the product distribution was carried out using two, F.I.D. capillary chromatographs. The GC area percent values are given in Table V.

TABLE V

| Chromatograph | Product Analysis (Area percent by G. C.)⁽ᵃ⁾ | | | | Avg. Br/DPO |
|---|---|---|---|---|---|
| | Pentabrom | Hexabrom | Heptabrom | Octabrom | |
| 1 | 5.09 | 91.00 | 3.84 | 0.07 | 5.99 |
| 2 | 5.97 | 90.99 | 3.05 | trace | 5.97 |

⁽ᵃ⁾Based on other hexabrom analyses, the results from chromatograph #1 appear to be slightly in error.

Examples 9–11 show that high selectivity to hexabrom was achieved at the specified reaction temperature.

EXAMPLES 12–13

Two additional runs were conducted generally as described above in which diphenyl oxide was added portionwise to 100 mole percent excess bromine using ZrCl₄ catalyst. The conditions used and results obtained are summarized in Table VI.

TABLE VI

| Ex. No. | Wt. % Cat on DPO | React. Temp. °C. | DPO Add'n Time (Hrs) | Ride Time (Hrs) | Product Analysis (Area percent by G. C.) | | | |
|---|---|---|---|---|---|---|---|---|
| | | | | | Pentabrom | Hexabrom | Heptabrom | Octabrom |
| 12 | 3 | 23 | 0.5 | 2.7 | 10.6 | 86.2 | 2.8 | Trace |
| | | | | 4.2 | 4.4 | 91.6 | 3.7 | 0.051 |
| | | | | 5.2 | 2.7 | 93.1 | 3.9 | 0.064 |
| | | | | 7.0 | 2.1 | 94.0 | 3.75 | 0.073 |
| 13 | 6 | 20–21 | 0.5 | 2.0 | 8.9 | 88.6 | 2.2 | Trace |
| | | | | 3.0 | 3.3 | 93.4 | 3.0 | 0.044 |
| | | | | 4.0 | 2.2 | 93.9 | 3.6 | 0.07 |
| | | | | 5.5 | 1.7 | 93.7 | 4.36 | 0.096 |
| | | | | 7.0 | 1.4 | 93.2 | 5.25 | 0.14 |

The results of Examples 12 and 13 show that even with extended reaction times very little change in product distribution occurs so long as the temperature is suitably controlled.

The partially brominated non-condensed ring aromatics are useful as flame retardants in a wide variety of organic materials such as polyethylene, polypropylene, polyesters, acrylonitrilebutadiene-styrene terpolymer, styrene, high impact polystyrene, styrene-butadiene copolymer, styrene-maleic anhydride copolymer, polyphenylene ethers and blends of the above. The amount used is generally an amount to provide about 5–15 weight percent bromine to the polymer. Synergists, such as antimony oxide, are routinely included.

Variations are possible within the spirit and scope of the appended claims.

What is claimed is:

1. A process for making a partially brominated non-condensed ring polyaromatic other than a polyphenylene ether, said process comprising reacting polyaromatic with bromine in the presence of a catalytic amount of a zirconium halide catalyst at a temperature from about 10° C. up to reflux wherein said process is conducted using about 5–24 moles of bromine for each equivalent weight of said polyaromatic wherein said equivalent weight is the molecular weight of the polyaromatic divided by the number of benzene rings in said polyaromatic.

2. A process of claim 1 conducted in the substantial absence of a solvent other than liquid bromine.

3. A process of claim 2 conducted by adding the polyaromatic to the liquid bromine containing the zirconium halide catalyst.

4. A process of claim 3 wherein said zirconium halide is introduced into said bromine in the form of zirconium chloride.

5. A process for making brominated diphenyl ether which contains an average of about 6 bromine atoms per molecule, said process comprising adding about 1 mole of molten diphenyl ether to at least about 9 moles of liquid bromine containing a catalytic amount of a zirconium halide and keeping the temperature of the reaction mixture at from ambient up to about 30° C. substantially throughout the entire reaction period.

6. A process of claim 5 wherein said reaction temperature is kept substantially within the range of about 20° to about 26° C. throughout substantially the entire reaction period.

7. A process of claim 6 wherein said zirconium halide is introduced into said bromine in the form of zirconium chloride.

8. A process of claim 5 wherein there are about 10.5 to about 12 moles of liquid bromine per mole of diphenyl ether added.

9. A process of claim 8 wherein said reaction temperature is kept substantially within the range of about 20° to about 26° C. throughout substantially the entire reaction period and wherein said zirconium halide is introduced into said bromine in the form of zirconium chloride.

* * * * *